(12) United States Patent
Zhou

(10) Patent No.: US 12,238,178 B2
(45) Date of Patent: Feb. 25, 2025

(54) EXERCISE DATA PROCESSING METHOD AND APPARATUS

(71) Applicant: Petal Cloud Technology Co., Ltd, Dongguan (CN)

(72) Inventor: Feng Zhou, Nanjing (CN)

(73) Assignee: PETAL CLOUD TECHNOLOGY CO., LTD., Dongguan (CN)

( * ) Notice: Subject to any disclaimer, the term of this patent is extended or adjusted under 35 U.S.C. 154(b) by 633 days.

(21) Appl. No.: 17/311,184

(22) PCT Filed: Nov. 27, 2019

(86) PCT No.: PCT/CN2019/121149
§ 371 (c)(1),
(2) Date: Jun. 4, 2021

(87) PCT Pub. No.: WO2020/114286
PCT Pub. Date: Jun. 11, 2020

(65) Prior Publication Data
US 2021/0377346 A1    Dec. 2, 2021

(30) Foreign Application Priority Data

Dec. 6, 2018 (CN) .......................... 201811489510.4

(51) Int. Cl.
*H04L 67/141* (2022.01)
*A63B 22/02* (2006.01)
*A63B 24/00* (2006.01)
*A63B 71/06* (2006.01)
*G16H 20/30* (2018.01)
(Continued)

(52) U.S. Cl.
CPC ............ *H04L 67/141* (2013.01); *A63B 22/02* (2013.01); *A63B 24/0062* (2013.01); *A63B 71/0622* (2013.01); *G16H 20/30* (2018.01); *G16H 40/67* (2018.01); *H04L 67/535* (2022.05); *H04W 4/80* (2018.02); *A63B 2225/50* (2013.01)

(58) Field of Classification Search
None
See application file for complete search history.

(56) References Cited

U.S. PATENT DOCUMENTS

2006/0063645 A1    3/2006    Chiang
2010/0285877 A1    11/2010   Corazza
(Continued)

FOREIGN PATENT DOCUMENTS

CN    101751802 A    6/2010
CN    102657517 A    9/2012
(Continued)

*Primary Examiner* — Phyllis A Book
(74) *Attorney, Agent, or Firm* — Conley Rose, P.C.

(57) ABSTRACT

An exercise device configured to obtain, from an exercise device server corresponding to the exercise device, user information corresponding to a user that uses the exercise device, wherein the user information has been entered and recorded by the user on an application client on a user terminal, has synchronized to an application server corresponding to the application client, and has sent from the application server to the exercise device server based on triggering by the application client, and process, based on the user information, a collected exercise parameter of the user to obtain exercise consumption data of the user.

20 Claims, 9 Drawing Sheets

(51) Int. Cl.
  *G16H 40/67* (2018.01)
  *H04L 67/50* (2022.01)
  *H04W 4/80* (2018.01)

(56) References Cited

U.S. PATENT DOCUMENTS

| | | | |
|---|---|---|---|
| 2013/0241696 | A1 | 9/2013 | Fabrizio |
| 2014/0156038 | A1* | 6/2014 | Poyhtari ................ G16H 40/67 |
| | | | 700/91 |
| 2014/0302967 | A1 | 10/2014 | Ashby et al. |
| 2015/0209617 | A1 | 7/2015 | Hsiao |
| 2015/0224364 | A1* | 8/2015 | Hsieh ................ A63B 24/0087 |
| | | | 700/275 |
| 2015/0382325 | A1* | 12/2015 | Johnson ................ H04W 72/04 |
| | | | 370/329 |
| 2017/0162069 | A1* | 6/2017 | Petakov ................... G09B 5/12 |
| 2017/0165524 | A1* | 6/2017 | Eder ................. A63B 21/0628 |
| 2018/0036591 | A1* | 2/2018 | King ......................... H04N 5/76 |
| 2020/0114207 | A1* | 4/2020 | Weldemariam ......... H04L 51/02 |
| 2021/0001180 | A1* | 1/2021 | Wang ..................... G06N 20/00 |
| 2021/0174971 | A1* | 6/2021 | Jain ........................ G16H 10/20 |
| 2021/0350923 | A1* | 11/2021 | McKirdy ............... G16H 40/67 |
| 2022/0249910 | A1* | 8/2022 | Hu ......................... G16H 50/70 |
| 2022/0395729 | A1* | 12/2022 | Toth ....................... G16H 40/63 |

FOREIGN PATENT DOCUMENTS

| | | |
|---|---|---|
| CN | 103679600 A | 3/2014 |
| CN | 103961839 A | 8/2014 |
| CN | 104606847 A | 5/2015 |
| CN | 104754028 A | 7/2015 |
| CN | 105164506 A | 12/2015 |
| CN | 206096849 U | 4/2017 |
| CN | 106693307 A | 5/2017 |
| CN | 106709636 A | 5/2017 |
| CN | 106934746 A | 7/2017 |
| CN | 107659627 A | 2/2018 |
| CN | 108261732 A | 7/2018 |
| CN | 108565000 A | 9/2018 |
| CN | 109769011 A | 5/2019 |
| EP | 3883211 A | 11/2019 |

\* cited by examiner

EXERCISE DATA PROCESSING METHOD AND APPARATUS

CROSS-REFERENCE TO RELATED APPLICATIONS

This application is a national stage of International Application No. PCT/CN2019/121149, filed on Nov. 27, 2019, which claims priority to Chinese Patent Application No. 201811489510.4, filed on Dec. 6, 2018. Both of the aforementioned applications are hereby incorporated by reference in their entireties.

TECHNICAL FIELD

This application relates to the field of intelligent control technologies, and in particular, to an exercise data processing method and apparatus.

BACKGROUND

Currently, as a user requirement continuously increases, an exercise device such as a treadmill gradually becomes intelligent and personalized, and becomes an exercise device that can calculate exercise consumption data (for example, consumed calories) for a user. However, the consumption data of the user is not only related to exercise parameters such as a distance and a time period of doing exercise by the user, but also related to the user, specifically, related to a weight, a gender, and the like of the user. In this case, to accurately obtain the exercise consumption data corresponding to the exercise done by the user, before an exercise device such as a treadmill is used, personal related information may be entered on the corresponding exercise device, so that the exercise device accurately calculates the exercise consumption data of the user.

However, the user manually enters the personal related information each time when using the exercise device. This not only easily discloses privacy of the user, but also results in complex operations for the user, making it inconvenient for the user to use the exercise device.

SUMMARY

To resolve the foregoing problem, embodiments of this application provide an exercise data processing method and apparatus, so that an exercise device can automatically obtain user information of a user, and more accurately calculate exercise consumption data of the user with reference to the user information and exercise parameters, to conveniently provide an accurate exercise data processing service for the user.

According to a first aspect, an embodiment of this application provides an exercise data processing method, used on a side of an exercise device, and specifically including: The exercise device obtains, from an exercise device server corresponding to the exercise device, user information corresponding to a user that uses the exercise device, where the user information is entered and recorded by the user on an application client on a user terminal, synchronized to an application server corresponding to the application client, and sent from the application server to the exercise device server based on triggering by the application client. The exercise device processes a collected exercise parameter of the user based on the user information, to obtain exercise consumption data of the user. In this way, by using an inherent connection relationship between the exercise device and the corresponding exercise device server, and a newly established connection between the exercise device server and the application server corresponding to the application client, the exercise device can obtain the user information that is recorded by the user on the application client on the user terminal and synchronized to the application server, so that the exercise device can specifically calculate accurate exercise consumption data of the user, and the user does not need to manually enter the user information on the exercise device during exercise, thereby facilitating processing of exercise data of the user on the exercise device, and improving exercise experience of the user.

In a possible implementation of the first aspect, the exercise device includes an information code, and the information code is scanned and parsed by the user terminal to obtain a device identifier of the exercise device, so that the user terminal is connected to the exercise device server corresponding to the device identifier, the exercise device server obtains, based on an application server identifier and a user identifier that are sent by the user terminal and from the application server corresponding to the application server identifier, the user information corresponding to the user identifier, and the exercise device obtains the user information from the exercise device server. This facilitates exchange of personalized information when the user uses the exercise device for exercise.

In another possible implementation of the first aspect, after the exercise device processes the collected exercise parameter of the user based on the user information, to obtain the exercise consumption data of the user, in a case, the exercise consumption data may be further sent to the exercise device server, so that the exercise device server sends the exercise consumption data to the application client by using the application server; in another case, the exercise consumption data may be alternatively displayed on a display of the exercise device. This can effectively provide convenience for the user, and improve user experience when the user uses the exercise device.

In still another possible implementation of the first aspect, the exercise device may further receive, through the established connection, recommendation information and/or a recommended service sent by the exercise device server. The exercise device displays the recommendation information and/or the recommended service on the display of the exercise device. The recommendation information and/or the recommended service are/is determined by the exercise device server based on a personal attribute of a user currently using the exercise device. The personal attribute is obtained by the exercise device server from the application server based on the established connection. In this way, the exercise device can automatically obtain the personal attribute of the user, analyze and predict possible interests and preferences of the user based on the personal attribute, and specifically provide the recommendation information and/or the recommended service, thereby improving the user's interest in exercise. This not only facilitates promotion of national fitness, but also improves user experience when the user uses the exercise device.

According to a second aspect, an embodiment of this application provides an exercise data processing method, used on a side of an exercise device server, and specifically including: First, the exercise device server receives a connection request triggered by an application client on a user terminal, and establishes a connection to an application server corresponding to an application server identifier, where the connection request is sent by the application client to the exercise device server corresponding to an exercise device after the application client determines the exercise device based on a device identifier of the exercise device, and the connection request carries a user identifier and the application server identifier corresponding to the application client. Then the exercise device server obtains, based on the connection, user information corresponding to the user identifier sent by the application server, where the user information is entered and recorded by a user on the application client on the user terminal and synchronized to the application server corresponding to the application client. Then the exercise device server sends the user information to the exercise device corresponding to the exercise device server, so that the exercise device processes, based on the user information, a collected exercise parameter of the user, to obtain exercise consumption data of the user.

In a possible implementation of the second aspect, after the exercise device server receives the connection request triggered by the application client on the user terminal, and before the exercise device server establishes the connection to the application server corresponding to the application server identifier, the exercise device server identifies the application server corresponding to the application server identifier, and determines whether an authorization relationship exists between an operator corresponding to the application server and an operator corresponding to the exercise device. If an authorization relationship exists, the exercise device server performs the "establishing a connection to an application server corresponding to an application server identifier"; or if no authorization relationship exists, the exercise device server sends, to the application client, Bluetooth pairing information corresponding to the exercise device, so that the application client establishes a Bluetooth connection to the exercise device based on the Bluetooth pairing information, and the exercise device obtains the user information from the application client through the Bluetooth connection. In this way, when no open interface is available between the two servers, the user can select a Bluetooth connection mode, thereby implementing diversified and flexible data exchange, and providing convenience for the user.

In another possible implementation of the second aspect, after the exercise device processes the collected exercise parameter of the user based on the user information, to obtain the exercise consumption data of the user, the exercise device server may further receive the exercise consumption data sent by the exercise device, and send the exercise consumption data to the application client by using the application server. The sending, by the exercise device server, the exercise consumption data to the application client by using the application server specifically includes: determining, in the stored application server identifier, a target application server identifier corresponding to the currently used exercise device; and determining an application server corresponding to the target application server identifier, and sending the exercise consumption data to the application server, so that the application server forwards the exercise consumption data to the application client.

In still another possible implementation of the second aspect, the exercise device server may further obtain, through the established connection, a personal attribute of a user currently using the exercise device, and push recommendation information and/or a recommended service to the exercise device based on the personal attribute, so that the exercise device plays the recommendation information and/or the recommended service for the user on a display. In this way, the exercise device can obtain the personal attribute of the user, analyze and predict possible interests and preferences of the user based on the personal attribute, and specifically provide the recommendation information and/or the recommended service, thereby improving the user's interest in exercise. This not only facilitates promotion of national fitness, but also improves user experience when the user uses the exercise device.

According to a third aspect, an embodiment of this application provides an exercise data processing method, used on a side of a user terminal, and specifically including: An application client on the user terminal sends, based on a device identifier of an exercise device to be used by a user, a connection request to an exercise device server corresponding to the exercise device, where the connection request carries a user identifier and an application server identifier corresponding to the application client, so that the exercise device server obtains, from an application server corresponding to the application server identifier, user information corresponding to the user identifier, and feeds back the user information to the exercise device, and the exercise device processes a collected exercise parameter of the user based on the user information, to obtain exercise consumption data of the user. The user information is entered and recorded by the user on the application client and synchronized to the application server corresponding to the application client. Then the application client on the user terminal receives the exercise consumption data sent by the application server. The exercise consumption data is sent by the exercise device to the application server by using the exercise device server.

In a possible implementation of the third aspect, the user terminal may further scan and parse an information code included in the exercise device, to obtain the device identifier of the exercise device.

It can be learned that a specific process of the exercise data processing method provided in this embodiment of this application includes: First, the application client on the user terminal sends, based on the device identifier of the exercise device to be used by the user, the connection request to the exercise device server corresponding to the exercise device, where the connection request carries the user identifier and the application server identifier corresponding to the application client. Then the exercise device server receives the connection request triggered by the application client on the user terminal, and establishes a connection to the application server corresponding to the application server identifier. Then the exercise device server sends, to the application server based on the established connection, the user information corresponding to the user identifier, and the exercise device server sends the received user information to the exercise device. Finally, the exercise device processes the collected exercise parameter of the user based on the user information, to obtain the exercise consumption data of the user. In this way, by using an inherent connection relationship between the exercise device and the corresponding exercise device server, and the newly established connection between the exercise device server and the application server corresponding to the application client, the exercise device can obtain the user information that is recorded by the user on the application client on the user terminal and synchronized to the application server, so that the exercise device can specifically calculate accurate exercise consumption data of the user, and the user does not need to manually enter the user information on the exercise device during exercise, thereby facilitating processing of exercise data of the user on the exercise device, and improving exercise experience of the user.

According to a fourth aspect, an embodiment of this application further provides another exercise data processing method, used on a side of an exercise device, and specifically including: First, the exercise device receives a Bluetooth pairing request sent by a user terminal, and establishes a Bluetooth connection to the user terminal by using a first Bluetooth module, where the Bluetooth pairing request is generated by the user terminal based on Bluetooth pairing information of the exercise device. Then the exercise device obtains, through the Bluetooth connection, user information sent by the user terminal, where the user information is entered by a user using the exercise device and is recorded and stored on an application client on the user terminal. Then the exercise device processes a collected exercise parameter of the user based on the user information, to obtain exercise consumption data of the user. In this way, the Bluetooth connection is established between the exercise device and the user terminal, so that the exercise device can obtain the user information recorded by the user on the application client on the user terminal, the exercise device can specifically calculate accurate exercise consumption data of the user, and the user does not need to manually enter the user information on the exercise device during exercise, thereby facilitating processing of exercise data of the user on the exercise device, and improving exercise experience of the user.

In a possible implementation of the fourth aspect, the exercise device includes an information code, and the information code is scanned and parsed by the user terminal to obtain a device identifier of the exercise device, so that the user terminal is connected to an exercise device server corresponding to the device identifier, to obtain the Bluetooth pairing information sent by the exercise device server. This facilitates exchange of personalized information when the user uses the exercise device for exercise.

In another possible implementation of the fourth aspect, after the exercise device obtains the exercise consumption data of the user, in a case, the exercise consumption data may be further sent to the application client through the Bluetooth connection, or the exercise consumption data may be displayed on a display of the exercise device. This can effectively provide convenience for the user, and improve user experience when the user uses the exercise device.

In still another possible implementation of the fourth aspect, the exercise device may further obtain, from the application client through the Bluetooth connection, a personal attribute of the user currently using the exercise device, and request, based on the personal attribute, the exercise device server to push recommendation information and/or a recommended service, to play the recommendation information and/or the recommended service for the user. In this way, the exercise device can automatically obtain the personal attribute of the user, analyze and predict possible interests and preferences of the user based on the personal attribute, and specifically provide the recommendation information and/or the recommended service, thereby improving the user's interest in exercise. This not only facilitates promotion of national fitness, but also improves user experience when the user uses the exercise device.

According to a fifth aspect, an embodiment of this application further provides another exercise data processing method, used on a side of a user terminal, and specifically including: First, the user terminal receives Bluetooth pairing information that corresponds to an exercise device and that is sent by an exercise device server. Then the user terminal sends a Bluetooth pairing request to a first Bluetooth module of the exercise device, and establishes a Bluetooth connection to the first Bluetooth module of the exercise device by using a second Bluetooth module. The Bluetooth pairing request is generated by the user terminal based on the Bluetooth pairing information of the exercise device. Then the user terminal sends user information to the exercise device through the Bluetooth connection, so that the exercise device processes a collected exercise parameter of a user based on the user information, to obtain exercise consumption data of the user. The user information is entered by the user using the exercise device and is recorded and stored on an application client on the user terminal.

In a possible implementation of the fifth aspect, the user terminal may further scan and parse an information code on the exercise device by using an image collection module, to obtain a device identifier of the exercise device.

In another possible implementation of the fifth aspect, the user terminal may further receive the exercise consumption data from the exercise device through the Bluetooth connection.

According to a sixth aspect, an embodiment of this application further provides another exercise data processing method, used on a side of an exercise device server, and specifically including: The exercise device server receives a Bluetooth pairing information request sent by an application client on a user terminal, where the Bluetooth pairing information request is sent by the application client to the exercise device server corresponding to an exercise device after the application client determines the exercise device based on a device identifier of the exercise device, and is used to request Bluetooth pairing information of the exercise device. The exercise device server sends the Bluetooth pairing information of the exercise device to the application client, so that the user terminal sends a Bluetooth pairing request to the exercise device, and establishes a Bluetooth connection to the exercise device. The Bluetooth pairing request is generated by the user terminal based on the Bluetooth pairing information of the exercise device. The user terminal sends user information to the exercise device through the Bluetooth connection, so that the exercise device processes a collected exercise parameter of a user based on the user information, to obtain exercise consumption data of the user. The user information is recorded and stored on the application client on the user terminal.

In a possible implementation of the sixth aspect, the exercise device server may further obtain, through the established Bluetooth connection, a personal attribute of a user currently using the exercise device, and push recommendation information and/or a recommended service to the exercise device based on the personal attribute, so that the exercise device plays the recommendation information and/or the recommended service for the user on a display of the exercise device.

It can be learned that a specific process of the exercise data processing method provided in this embodiment of this application includes: First, the application client on the user terminal requests, based on the device identifier of the exercise device to be used by the user, the Bluetooth pairing information corresponding to the exercise device from the exercise device server corresponding to the exercise device. Then the exercise device server sends, to the user terminal, the Bluetooth pairing information corresponding to the exercise device. The user terminal sends the Bluetooth pairing request to the exercise device, and establishes the Bluetooth connection to the exercise device. The Bluetooth pairing request is generated by the user terminal based on the Bluetooth pairing information of the exercise device. Then the user terminal sends the user information to the exercise device through the Bluetooth connection. Finally, the exercise device processes the collected exercise parameter of the user based on the user information, to obtain the exercise consumption data of the user. In this way, the Bluetooth connection is established between the exercise device and the user terminal, so that the exercise device can obtain the user information recorded by the user on the application client on the user terminal, the exercise device can specifically calculate accurate exercise consumption data of the user, and the user does not need to manually enter the user information on the exercise device during exercise, thereby facilitating processing of exercise data of the user on the exercise device, and improving exercise experience of the user.

According to a seventh aspect, an embodiment of this application further provides an exercise device, including a memory, a processor, and a transceiver. The memory stores one or more programs. When the processor executes the one or more programs, the exercise device is enabled to perform the steps of any method in the first aspect and/or the fourth aspect.

According to an eighth aspect, an embodiment of this application further provides an exercise device server, including a memory, a processor, and a transceiver. The memory stores one or more programs. When the processor executes the one or more programs, the exercise device server is enabled to perform the steps of any method in the second aspect and/or the fifth aspect.

According to a ninth aspect, an embodiment of this application further provides a user terminal, including a memory, a processor, and a transceiver. The memory stores one or more programs. When the processor executes the one or more programs, the user terminal is enabled to perform the steps of any method in the third aspect and/or the sixth aspect.

According to a tenth aspect, an embodiment of this application provides a computer-readable storage medium. The computer-readable storage medium stores an instruction. When the instruction is run on a computer, the computer is enabled to perform the methods in the foregoing aspects.

According to an eleventh aspect, an embodiment of this application provides a computer program product including an instruction. When the computer program product is run on a computer, the computer is enabled to perform the methods in the foregoing aspects.

BRIEF DESCRIPTION OF DRAWINGS

To describe the technical solutions in the embodiments of this application more clearly, the following briefly describes the accompanying drawings for describing the embodiments. It is clearly that the accompanying drawings in the following description show merely some embodiments recorded in this application, and an ordinary person skilled in the art may derive other drawings from these accompanying drawings.

DESCRIPTION OF EMBODIMENTS

Figure 1:
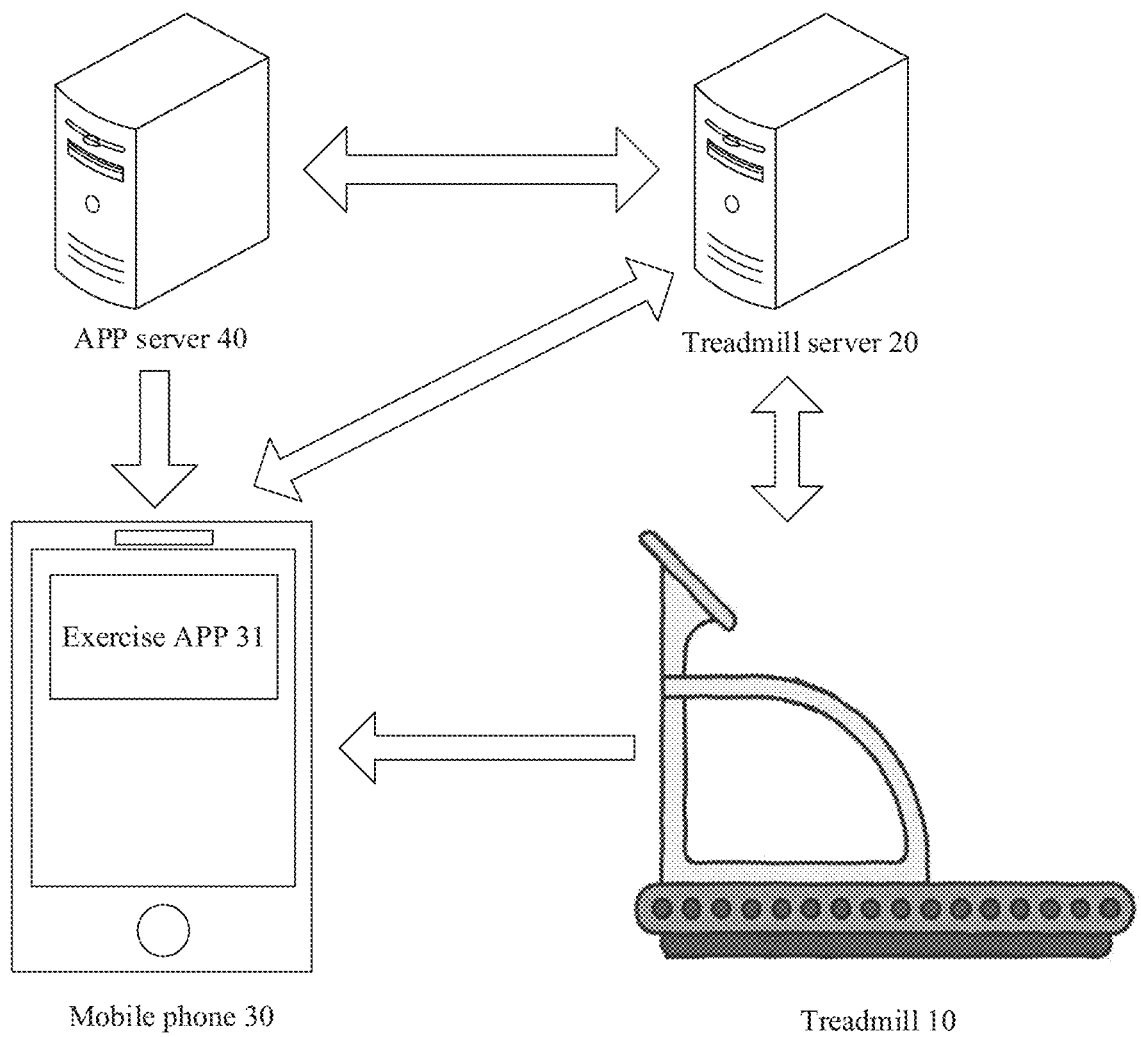
FIG. 1 is a schematic diagram of a system framework in an application scenario according to an embodiment of this application.

Currently, exercise devices (for example, fitness devices such as treadmills and stationary bikes, and medical devices used for rehabilitation) gradually become intelligent and personalized to meet increasing user requirements. An exercise device may not only record exercise parameters of a user, for example, record an exercise time, an exercise speed, and an exercise distance when the user uses the exercise device, but also calculate exercise consumption data of the user, for example, calculate calories consumed each time the user uses the exercise device, so that the user learns of calorie intakes and consumption in the user's body, and properly controls and plans a balance between diet and exercise to keep healthy.

However, the exercise consumption data of the user is not only related to the exercise parameters such as the exercise distance and the exercise time of the user, but also related to the user, specifically, related to user information such as a weight and a gender of the user. In this case, to accurately obtain the exercise consumption data generated when the user does exercise, the exercise device needs to obtain the user information of the user. A public exercise device, for example, a treadmill in a gym, is used by different users in different periods of time. If a user does not set personal user information, inaccurate exercise consumption data is displayed based on a default value and a collected exercise parameter, so that user experience when the user uses the treadmill is poor. If the user wants to obtain accurate exercise consumption data, the user may manually enter personal user information on the treadmill before running on the treadmill, so that the treadmill can specifically and accurately calculate and output exercise consumption data of the user.

It can be learned that the user needs to manually enter the user information, so that the exercise device accurately outputs the exercise consumption data corresponding to exercise done by the user. In one aspect, personal privacy of the user is easily disclosed. In another aspect, the user enters the user information of the user each time when using the exercise device for exercise, resulting in complex operations of using the exercise device, and greatly degrading user experience when the user uses the exercise device.

In view of this, to overcome a problem that a user needs to manually enter user information on an exercise device to obtain accurate exercise consumption data when using the exercise device, and improve user experience when the user uses the exercise device, the embodiments of this application provide an exercise data processing method, so that a user may enter user information of the user on an application client installed on a user terminal (for example, a mobile phone) of the user, and store the user information of the user on the application client. In this case, when the user needs to use the exercise device for exercise, the exercise device may automatically obtain the user information of the user, and the user does not need to manually enter the user information each time when using the exercise device. This not only ensures security of the user's personal information, but also can specifically calculate and output accurate exercise consumption data of the user, thereby improving user experience when the user uses the exercise device for exercise.

In a first possible implementation, if the user needs to use the exercise device for exercise, the exercise device may obtain, through an inherent connection between the exercise device and an exercise device server corresponding to the exercise device, the user information pre-recorded and stored by the user. A specific process may be as follows: The to-be-used exercise device is determined by using a device identifier, of the to-be-used exercise device, that is obtained by the application client. A connection request is sent to the exercise device server corresponding to the exercise device, where the connection request carries a user identifier and an identifier of the application client, and requests the exercise device server to establish a connection to an application server corresponding to the application client, so that the exercise device server may obtain the user information from the application server and feed back the user information to the exercise device corresponding to the exercise device server, and the exercise device may process a collected exercise parameter by using the user information, to obtain accurate exercise consumption data of the user. In this way, the user does not need to manually enter the user information on the exercise device, and the exercise device may automatically obtain the user information of the user from the exercise device server corresponding to the exercise device, and output the accurate exercise consumption data, thereby improving user experience.

In a second possible implementation, if the user needs to use the exercise device for exercise, the exercise device may obtain, by establishing a Bluetooth connection to the user terminal (for example, the mobile phone) of the user, the user information from the application client installed on the user terminal. A specific process may be as follows: The to-be-used exercise device is determined by using a device identifier, of the to-be-used exercise device, that is obtained by the application client. Bluetooth pairing information of the exercise device is requested from an exercise device server corresponding to the exercise device. After the application client obtains the Bluetooth pairing information fed back by the exercise device server, the user terminal generates a Bluetooth pairing request based on the Bluetooth pairing information, and sends the Bluetooth pairing request to the exercise device to establish a Bluetooth connection to the exercise device, so that the exercise device may obtain the user information from the application client on the user terminal through the Bluetooth connection, and the exercise device may process a collected exercise parameter by using the user information, to obtain accurate exercise consumption data of the user. In this way, the user does not need to manually enter the user information on the exercise device, and the exercise device may automatically obtain the user information of the user from the user terminal through the established Bluetooth connection, and output the accurate exercise consumption data, thereby improving user experience.

With reference to the accompanying drawings and by using embodiments, the following describes in detail specific implementations of the exercise data processing method provided in the embodiments of this application.

For example, in a scenario in the embodiments of this application, the first possible implementation may be used in a scenario shown in FIG. 1. In the scenario, the exercise device is a treadmill 10, the exercise device server is a treadmill server 20 corresponding to the treadmill 10, the user terminal is a mobile phone 30 of a user, the application client is an exercise APP 31 installed on the mobile phone 30, and the application server is an APP server 40 corresponding to the exercise APP 31. The treadmill 10 and the treadmill server 20 have an inherent connection, and may exchange data. In addition, the exercise APP 31 and the APP server 40 also have an inherent connection, and may exchange data. In addition, after the user downloads and installs the exercise APP 31 on the mobile phone 30, when registering an account or completing personal information, the user may enter and store user information of the user, for example, information such as an age, a gender, a height, and a weight. The user information is synchronously stored on the APP server 40. In addition, an information code (for example, a two-dimensional code) may be further displayed on the treadmill 10, so that the user can obtain information when using the treadmill 10.

A specific exercise data processing solution may include: A user A wants to use the treadmill 10. First, the user A powers on the treadmill 10, and scans the information code on the treadmill 10 by using the exercise APP 31 on the mobile phone 30, so that the exercise APP 31 obtains a device identifier aaaa of the treadmill 10. Then the exercise APP 31 determines, by using the aaaa, that a to-be-used treadmill is the treadmill 10, and sends a connection request to the treadmill server 20 corresponding to the treadmill 10, to request the treadmill server 20 to establish a connection to the APP server 40. After the connection is established, the treadmill server 20 requests the APP server 40 to return user information of the user A. Then, after receiving the user information bbbb of A from the APP server 40, the treadmill server 20 feeds back the user information bbbb to the corresponding treadmill 10. Finally, the treadmill 10 processes, based on the user information bbbb, an exercise parameter of A that is collected in real time, to obtain real-time exercise consumption data of A until A completes running on the treadmill 10. The treadmill 10 generates total exercise consumption data of A for the running.

It should be noted that the treadmill server 20 in the scenario is a network-side management device corresponding to the treadmill 10, and may be a specific service device, or may be a cloud service device. Similarly, the APP server 40 is a network-side management device corresponding to the exercise APP 31, and may be a specific service device, or may be a cloud service device. This is not specifically limited in this embodiment of this application.

It can be understood that the foregoing scenario is merely an example of a scenario provided in the embodiments of this application, and the embodiments of this application are not limited to the scenario.

Before the first possible implementation is described, an exercise data processing apparatus for performing the implementation is first described. Hardware structures of an exercise device 200 related to the exercise data processing apparatus, an exercise device server 300 corresponding to the exercise device, and a user terminal 400 are specifically described.

It should be noted that the exercise device 200 may be a fitness device used by a user, for example, a treadmill, or may be a medical rehabilitation device used by a user for rehabilitation treatment. The exercise device 200 and the exercise device server 300 may exchange data, and specifically, may establish a connection and communicate with each other by using a telecommunications network. The exercise device server 300 is a network-side device that serves the exercise device 200, and specifically, may be a physical server corresponding to the exercise device 200, or may be a cloud server that serves the exercise device 200. The user terminal 400 may be a mobile phone, a tablet computer, an iPad, a wearable intelligent terminal, or the like of a user. Any terminal on which an application client (for example, a Codoon exercise APP) can be installed may serve as the user terminal 400. The user terminal 400 may also exchange, by using an application client, data with an application server corresponding to the user terminal 400.

Figure 2:
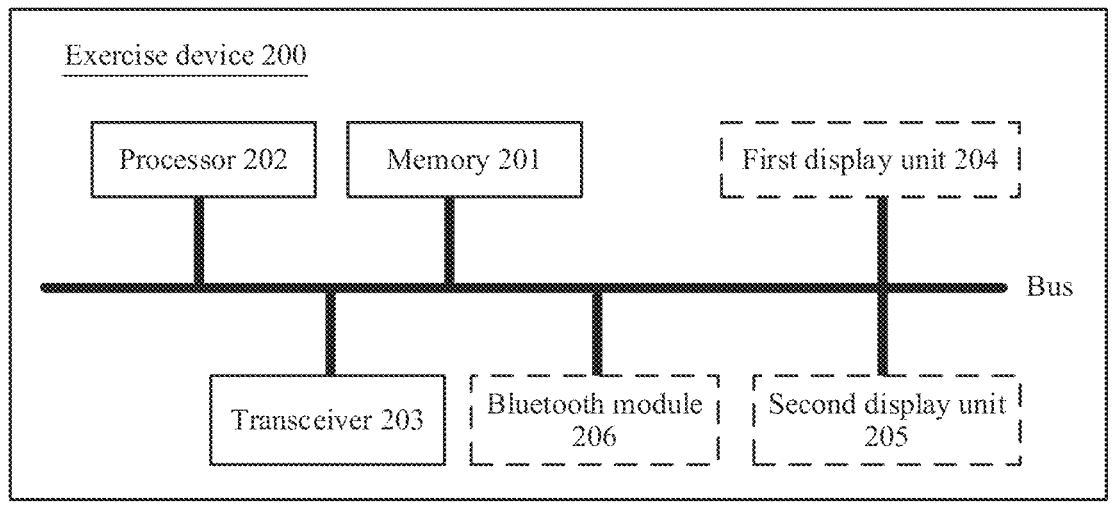
FIG. 2 is a schematic structural diagram of an exercise device according to an embodiment of this application.

For the exercise device 200, FIG. 2 is a schematic structural diagram of an exercise data processing apparatus according to an embodiment of this application. Referring to FIG. 2, the exercise device 200 may include a memory 201, a processor 202, and a transceiver 203. The processor 202 in the exercise device 200 is configured to read a software instruction in the memory 201, and execute the software instruction to implement the corresponding operations performed by the exercise device 200 in the first possible implementation provided in the embodiments of this application. In addition, the exercise device 200 may further include a first display unit 204 and a second display unit 205. The first display unit 204 and the second display unit 205 may be one display on the exercise device 200, or may be two different displays on the exercise device 200. The display on the exercise device 200 may be a display delivered together with the exercise device 200, or may be a display that is subsequently installed on the exercise device 200 and that can exchange data with the exercise device 200. Optionally, the exercise device may further include a Bluetooth module 206. The Bluetooth module 206 provides a Bluetooth function for the exercise device 200, and is configured to perform Bluetooth communication with another device (for example, the user terminal 400) that has a Bluetooth module.

Figure 3:
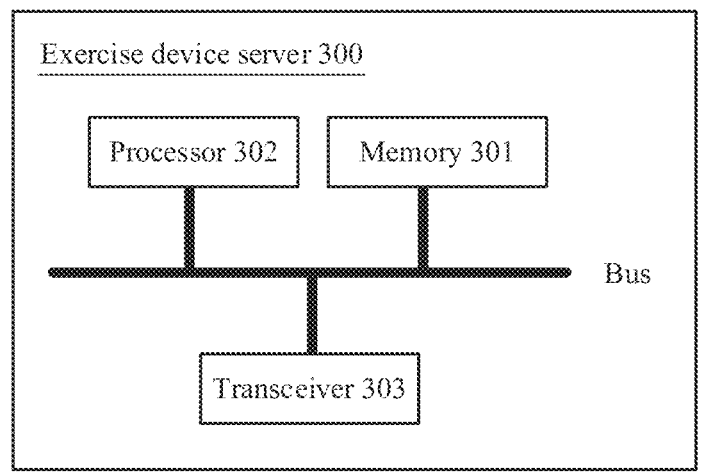
FIG. 3 is a schematic structural diagram of an exercise device server according to an embodiment of this application.

For the exercise device server 300, FIG. 3 is a schematic structural diagram of an exercise data processing apparatus according to an embodiment of this application. Referring to FIG. 3, the exercise device server 300 may include a memory 301, a processor 302, and a transceiver 303. The processor 302 in the exercise device server 300 is configured to read a software instruction in the memory 301, and execute the software instruction to implement the corresponding operations performed by the exercise device server 300 in the first possible implementation provided in the embodiments of this application.

Figure 4:
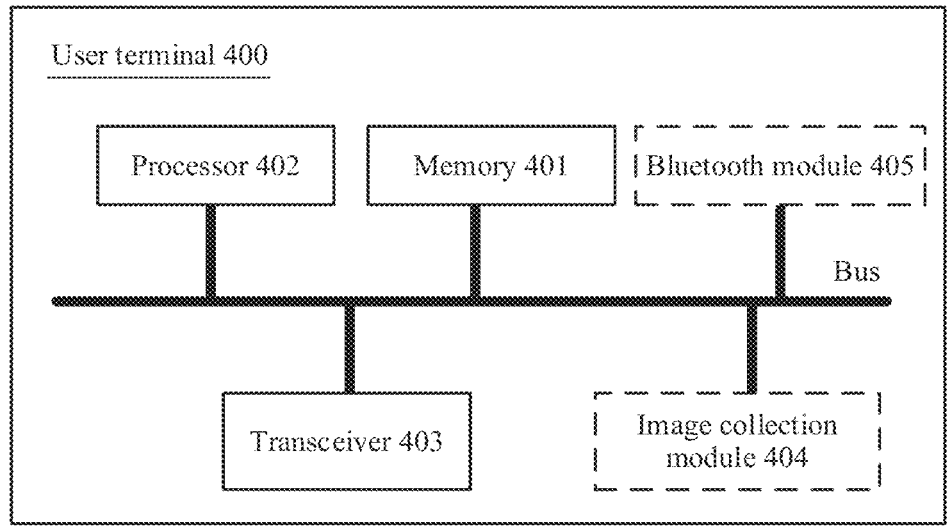
FIG. 4 is a schematic structural diagram of a user terminal according to an embodiment of this application.

For the user terminal 400, FIG. 4 is a schematic structural diagram of an exercise data processing apparatus according to an embodiment of this application. Referring to FIG. 4, the user terminal 400 may include a memory 401, a processor 402, and a transceiver 403. The processor 402 in the user terminal 400 is configured to read a software instruction in the memory 401, and execute the software instruction to implement the corresponding operations performed by the user terminal 400 in the first possible implementation provided in the embodiments of this application. In addition, the user terminal 400 may further include an image collection module 404. The image collection module 404 may be a camera integrated on the user terminal 400, or may be an independent camera that can exchange data with the user terminal 400. Optionally, the user terminal 400 further includes a Bluetooth module 405. The Bluetooth module 405 provides a Bluetooth function for the user terminal 400, and is configured to perform Bluetooth communication with another device (for example, the exercise device 200) that has a Bluetooth module.

Figure 5:
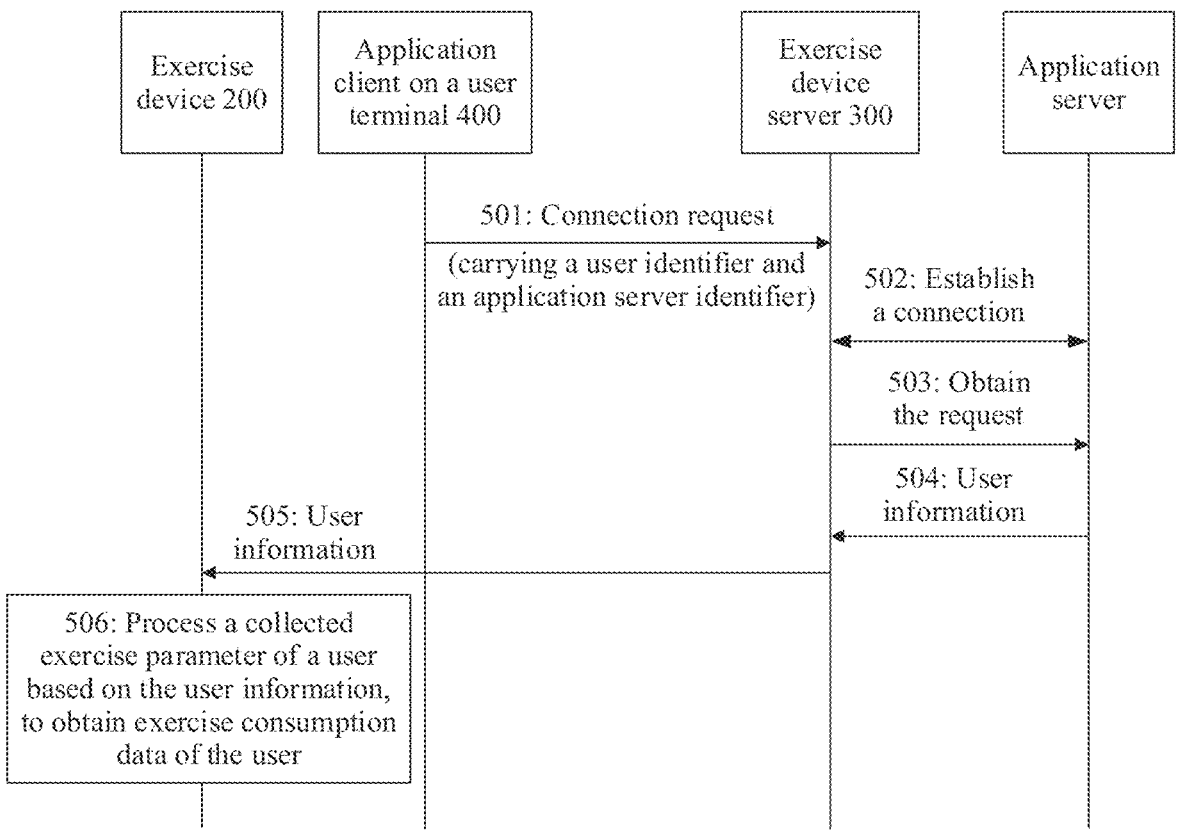
FIG. 5 is a signaling flowchart of an exercise data processing method according to an embodiment of this application.

FIG. 5 is a schematic signaling flowchart of an exercise data processing method according to an embodiment of this application. Referring to FIG. 5, the exercise data processing method corresponds to the first possible implementation, and specifically includes step 501 to step 505.

Step 501: An application client on a user terminal 400 sends, based on a device identifier of an exercise device 200 to be used by a user, a connection request to an exercise device server 300 corresponding to the exercise device 200, where the connection request carries a user identifier and an application server identifier corresponding to the application client.

It can be understood that the exercise device 200 is a device that can be used by the user to achieve an exercise effect and consume calories in the user's body, and may specifically include a fitness device such as a treadmill or a stationary bike, and a medical device such as a weight loss gait trainer. The device identifier of the exercise device 200 indicates an identifier that can uniquely identify the exercise device 200, and may be specifically a device number of the exercise device 200 at delivery, a use number of the exercise device 200 when the exercise device 200 is put into use by an operator, or the like. The exercise device server 300 corresponding to the exercise device 200 is configured to serve the exercise device 200, and is a network-side management device that processes a service of the exercise device 200, and may be specifically a physical service device corresponding to the exercise device or a cloud server corresponding to the exercise device.

The application client on the user terminal 400 is a third-party exercise APP installed on the user terminal, for example, a Codoon exercise APP or a Huawei health APP, and is configured to monitor an exercise status of the user and record data generated during exercise of the user, and may be considered as an "exercise manager" of the user. Different application clients may correspond to different application servers. An application server is configured to serve an application client corresponding to the application server, and is a network-side management device that processes a service of the application client, and may be specifically a physical service device corresponding to the application client or a cloud server corresponding to the application client.

The exercise device 200 and the exercise device server 300 have an inherent connection, and may exchange data. In addition, the application client and the application server also have an inherent connection, and may exchange data.

During specific implementation, when the user needs to use the exercise device 200 for exercise, step 501 may specifically include: Step 1: The user may power on the exercise device 200 by tapping a power-on button of the exercise device 200 or the like. Step 2: The user may obtain the device identifier of the exercise device 200 by using the application client installed on the user terminal of the user. Step 3: The application client determines the to-be-used exercise device 200 based on the obtained device identifier, and generates the connection request based on the user identifier and an application client identifier. Step 4: The application client sends the connection request to the exercise device server 300 corresponding to the determined to-be-used exercise device 200.

In some possible implementations, the device identifier of the exercise device 200 may be carried in an information code, and the information code may be specifically a two-dimensional code or a bar code. The exercise device 200 may display, on the exercise device 200, the information code that carries the device identifier. A display manner specifically includes: In a case, the information code may be static, that is, one exercise device corresponds to a fixed information code. In this case, the information code may be posted on the exercise device. In another case, to ensure security and reliability of data transmission, the information code may dynamically change, that is, different information codes are displayed as time changes. In this case, the information code may be displayed on a display of the exercise device 200 or an external display device connected to the exercise device. In this case, the information code not only carries the device identifier of the exercise device 200, but may also carry a timestamp at which the information code is generated.

In an example, step 2 of step 501 may be specifically as follows: The user scans, by using an image collection module 404 and the application client installed on the user terminal 400, the information code displayed on the exercise device 200, and parses the information code to obtain the device identifier of the exercise device 200.

In another example, step 2 of step 501 may be specifically as follows: After the user scans, by using the image collection module 404 and another client that has a code scanning function and that is installed on the user terminal 400, for example, an instant messaging client, the information code displayed on the exercise device 200, in a case, the code scanning client may directly parse the information code to obtain the device identifier of the exercise device 200, and send, in response to a trigger operation of the user, the device identifier to the application client that is installed on the user terminal 400 and that is configured to record exercise data. In another case, alternatively, the code scanning client may send, to the application client that is installed on the user terminal 400 and that is configured to record exercise data, the information code obtained by scanning the code, and the application client parses the information code to obtain the device identifier of the exercise device 200.

It can be understood that, when obtaining the device identifier of the exercise device 200, the application client may determine, based on the device identifier, the exercise device 200 that the user currently wants to use, and may also determine a receiver of the connection request generated by the application client, that is, the exercise device server 300 corresponding to the exercise device 200.

The connection request carries the user identifier and the application server identifier corresponding to the application client, and is used to request the exercise device server 300 to establish a connection to the application server of the application client corresponding to the application client identifier, and notify the exercise device server 300 that to-be-obtained user information is user information of the user corresponding to the user identifier.

The application client is triggered to send the connection request to the exercise device server 300 according to step 501. This not only provides a trigger condition for establishing the connection between the exercise device server 300 and the application server, but also notifies the exercise device server 300 of a target object to which the exercise device server 300 should establish the connection and target information to be obtained after the connection is established, thereby providing a data basis for a subsequent step.

Step 502: The exercise device server 300 receives the connection request triggered by the application client on the user terminal 400, and establishes the connection to the application server corresponding to the application server identifier.

It can be understood that step 502 may be specifically as follows: After a transceiver 303 of the exercise device server 300 receives the connection request, a processor 302 of the exercise device server 300 establishes the connection to the application server corresponding to the application server identifier.

It can be understood that, after receiving the connection request, the exercise device server 300 may parse the connection request to obtain the application client identifier and the user identifier that are carried in the connection request. In this case, the exercise device server 300 may determine the corresponding application client based on the application client identifier, to determine the application server corresponding to the application client. In this case, the exercise device server 300 responds to the connection request, and requests to establish the connection to the determined application server, to facilitate subsequent data exchange.

For subsequent data exchange, the exercise device server 300 may further store the application client identifier and the user identifier that are obtained by parsing the connection request.

Figure 6:
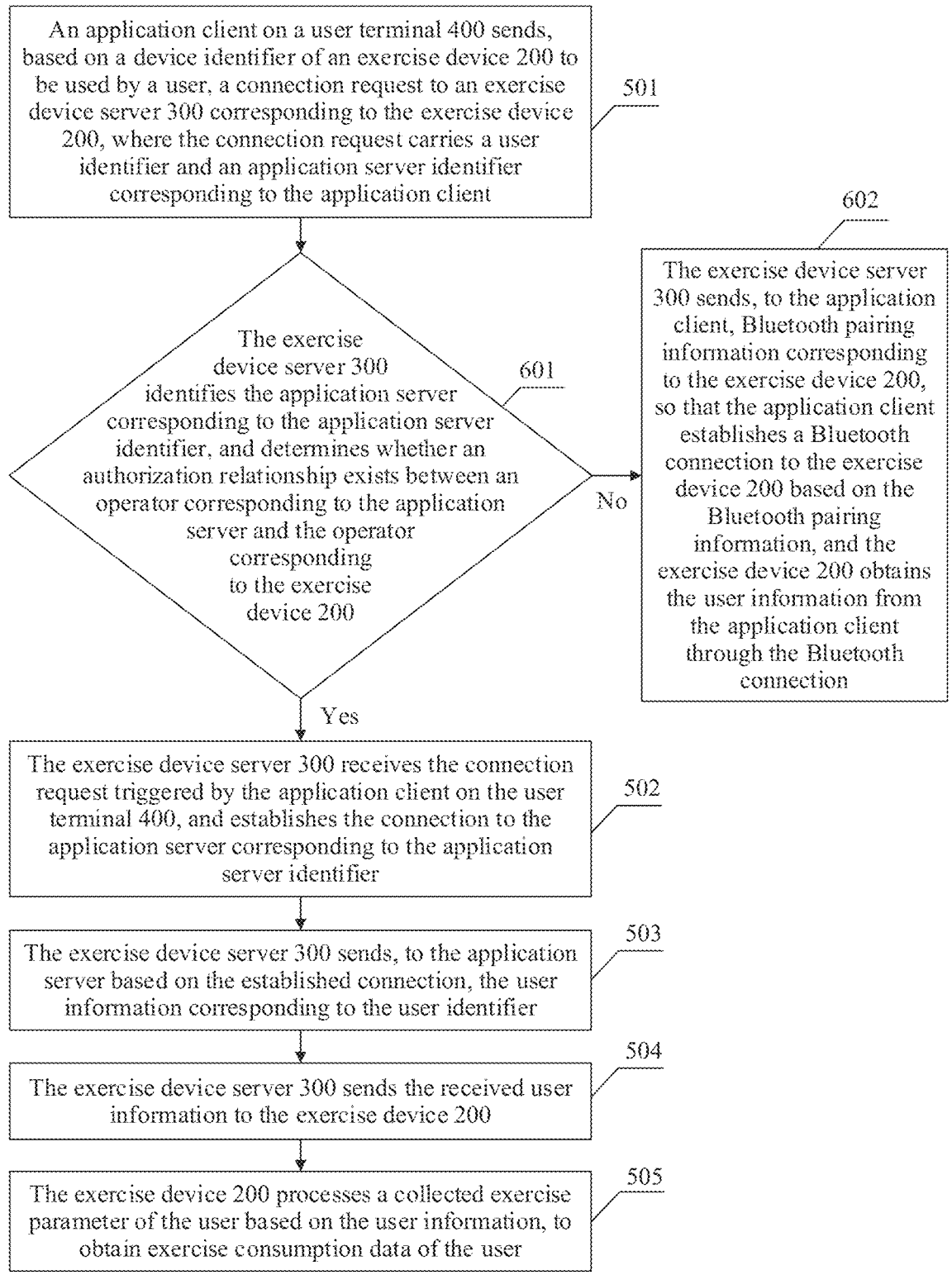
FIG. 6 is a schematic flowchart of an example of an exercise data processing method according to an embodiment of this application.

During specific implementation, there are a plurality of exercise device operators, and there are also a plurality of operators of applications used to record exercise data. Therefore, for security of data exchange, data exchange between operators may be allowed through authorization. If data exchange is allowed between an operator of the exercise device 200 and an operator of an application, authorization may be performed on each other, and an authorization relationship is stored. When access is required, an interface may be opened to each other. If data exchange is not allowed between the operator of the exercise device 200 and the operator of the application, no corresponding authorization relationship exists. In this case, FIG. 6 is a schematic flowchart of an example according to an embodiment of this application. After step 501 and before step 502, this embodiment of this application may further include the following steps.

Step 601: The exercise device server 300 identifies the application server corresponding to the application server identifier; determines whether an authorization relationship exists between an operator corresponding to the application server and the operator corresponding to the exercise device 200; and if an authorization relationship exists, performs step 502; or if no authorization relationship exists, performs step 602.

Step 602: The exercise device server 300 sends, to the application client, Bluetooth pairing information corresponding to the exercise device 200, so that the application client establishes a Bluetooth connection to the exercise device 200 based on the Bluetooth pairing information, and the exercise device 200 obtains the user information from the application client through the Bluetooth connection.

It can be understood that step 601 and step 602 may be specifically as follows: The processor 302 of the exercise device server 300 identifies the application server corresponding to the application server identifier, and determines whether an authorization relationship exists between the operator corresponding to the application server and the operator corresponding to the exercise device 200. If no authorization relationship exists, the transceiver 303 of the exercise device server 300 sends, to the application client on the user terminal 400, the Bluetooth pairing information corresponding to the exercise device 200, so that the application client establishes the Bluetooth connection to the exercise device 200 based on the Bluetooth pairing information, and the exercise device 200 obtains the user information from the application client through the Bluetooth connection.

It should be noted that step 602 is specifically exchanging data through the Bluetooth connection established between the exercise device 200 and the user terminal 400. For a specific implementation, refer to the related descriptions in the second possible implementation. Details are not described herein again.

It should be noted that step 602 is performed in a condition in which no authorization relationship exists between the operator corresponding to the application server and the operator corresponding to the exercise device 200; or step 602 may be performed in another condition, for example, when the user actively selects a Bluetooth connection mode, or when network quality in an environment in which the exercise device 200 is located is comparatively poor.

Step 503: The exercise device server 300 sends, to the application server based on the established connection, the user information corresponding to the user identifier.

It should be noted that, after establishing the connection to the application server, the exercise device server 300 may request the user information corresponding to the user identifier from the application server. However, to ensure that the user can control distribution of the user information of the user, the application server needs to obtain an indication from the user before sending the user information to the exercise device server 300. If the user uses the exercise device corresponding to the exercise device server 300 for exercise, when the exercise device server 300 requests the user information from the application server, the processor 302 may first determine whether the user uses the exercise device corresponding to the exercise device server 300 for the first time. If yes, the application server may guide, by using a standard authorization procedure (for example, an Oauth 2.0 authorization procedure), the user to authorize the exercise device server 300 on the application client of the user according to willingness of the user, determine, in information about user authorization allowed during the authorization, information requested by the exercise device server 300 as the user information, and send the user information to the exercise device server 300. If the user uses the exercise device corresponding to the exercise device server 300 not for the first time, that is, the user has authorized the exercise device server 300 on the application client of the user, the application server may determine the user information based on the existing authorization, and send the user information to the exercise device server 300. In this way, the user information of the user may be shared under awareness of the user, thereby ensuring that the user can protect personal information of the user, and improving user experience on a basis of protecting user privacy.

During specific implementation, after establishing the connection to the application server, the exercise device server 300 may generate an obtaining request based on the user identifier obtained by parsing the connection request. The obtaining request may carry the user identifier, and is used to request to obtain the user information of the user corresponding to the user identifier from the application server.

It can be understood that the user information may include at least one piece of the following information: an age, a gender, a height, a weight, and the like. The requested user information may be determined according to a pre-specified setting, or the user may be indicated to select different indicators as the requested user information according to different requirements.

In an example, after receiving the obtaining request sent by the exercise device server 300, the application server may search data stored on the application server for the user information corresponding to the parsed-out user identifier, and return the found user information to the exercise device server 300.

In another example, to feed back more accurate user information to the exercise device server 300, that is, to feed back related user information that may be used by the exercise device 200 to calculate accurate exercise consumption data, after finding the user information corresponding to the parsed-out user identifier, the application server may further specifically select specified related user information from the user information, and then feed back the selected user information to the exercise device server 300.

Step 504: The exercise device server 300 sends the received user information to the exercise device 200.

It can be understood that the transceiver 303 of the exercise device server 300 sends the received user information to the exercise device 200. In this case, a transceiver 203 of the exercise device 200 may receive the user information.

Step 505: The exercise device 200 processes a collected exercise parameter of the user based on the user information, to obtain exercise consumption data of the user.

It can be understood that a processor 202 of the exercise device 200 may process the collected exercise parameter of the user based on the user information, to obtain the exercise consumption data of the user.

It can be understood that the exercise consumption data is calories consumed by the user during current exercise, for example, may be a value of the calories consumed. It should be noted that the exercise consumption data may be alternatively other exercise-related data for different exercise devices 200 and different requirements. Details are not described herein again.

The exercise parameter is exercise data that can be directly collected by the exercise device 200 when the user does exercise on the exercise device 200, and may be specifically an exercise time, an exercise distance, an exercise speed, and the like. For example, when the user runs on a treadmill, the collected exercise parameter may include running duration, a running speed, a running mileage, and the like.

During specific implementation, after obtaining the user information by using the exercise device server 300, the exercise device 200 may calculate the exercise consumption data of the user with reference to an exercise parameter recorded on the exercise device 200. A specific calculation manner may be determined according to different requirements, for example, different exercise devices and different user requirements for accuracy. In an example, assuming that the exercise consumption data is calories consumed during running, a calculation formula may be as follows: Calories consumed during running (kilocalorie)=Weight (kilogram)×Exercise time (hour)×[30/Exercise speed (minute/ 400 meters)]. It can be learned that, when the exercise time and the exercise speed are fixed, a heavier user consumes more calories during running, and contrarily, a lighter user consumes fewer calories during running. It should be noted that, if the exercise consumption data is calculated by using the foregoing calculation formula, only the weight of the user needs to be actively obtained as the user information, and only the exercise speed and the exercise time of the user need to be collected as the exercise parameter.

It should be noted that the age and the gender also have corresponding impact on the exercise consumption data of the user. For example, when other conditions are the same, larger exercise consumption data is generated for an older user, and contrarily, smaller exercise consumption data is generated for a younger user. For another example, when other conditions are the same, larger exercise consumption data is generated for a male user, and smaller exercise consumption data is generated for a female user.

It can be understood that, after step 505, to display comparatively accurate exercise consumption data obtained through processing to the user, in an example, the exercise device 200 may directly display the exercise consumption data on a first display unit 204, for example, the display of the exercise device 200 or the external display device connected to the exercise device 200, until the user stops using the exercise device 200 and powers off the exercise device 200.

Figure 7:
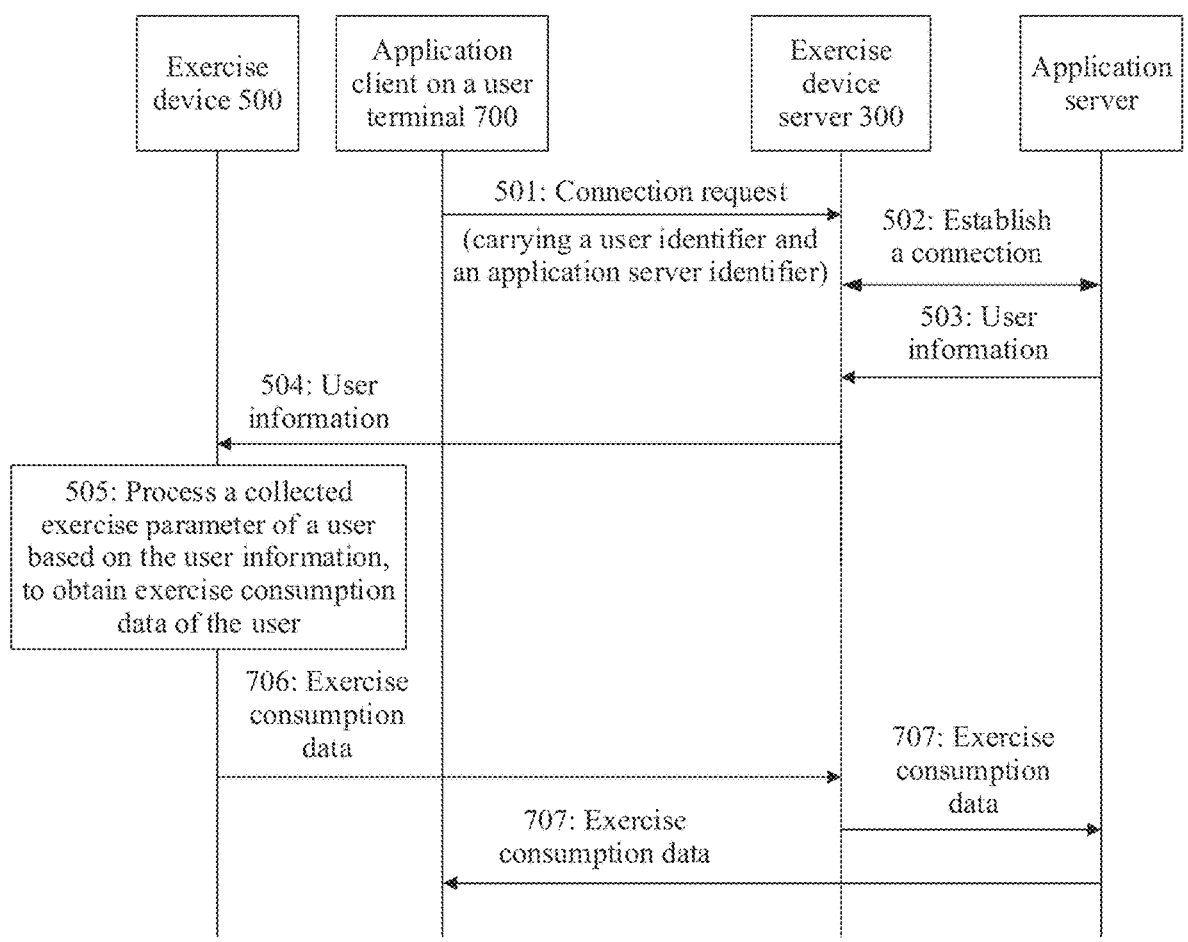
FIG. 7 is a signaling flowchart of another example of an exercise data processing method according to an embodiment of this application.

In another example, for many current application clients that are used to record an exercise status of a user, although the user may manually enter, on the application client, the exercise consumption data displayed on the exercise device 200, to facilitate use by the user and ensure comprehensiveness of exercise data, the exercise consumption data may be further automatically fed back to the application client in this embodiment of this application. In a schematic signaling flowchart shown in FIG. 7, after step 505, this embodiment of this application may further include the following steps.

Step 706: The exercise device 200 sends the exercise consumption data to the exercise device server 300.

Step 707: The exercise device server 300 sends the exercise consumption data to the application client by using the application server.

It can be understood that step 706 and step 707 may be specifically as follows: The transceiver 203 of the exercise device 200 sends the exercise consumption data to the exercise device server 300. After receiving the exercise consumption data, the transceiver 303 of the processor 302 of the exercise device server 300 may send the exercise consumption data to the application client by using the application server.

It can be understood that, when step 502 is performed, the exercise device server 300 establishes the connection to the application server corresponding to the application server identifier, and for subsequent data exchange, the exercise device server 300 may further store the application client identifier and the user identifier that are obtained by parsing the connection request. In this case, after the exercise device server 300 receives the exercise consumption data, step 707 may specifically include: First, the exercise device server 300 respectively determines, in stored application server identifiers and user identifiers, a target application server identifier and a target user identifier that correspond to the currently used exercise device 200. Then the exercise device server 300 determines a corresponding application server by using the target application server identifier, and sends the exercise consumption data to the determined application server. Then the application server determines, based on the target user identifier, an application client for receiving the exercise consumption data, and sends the exercise consumption data to the application client on a corresponding user terminal.

During specific implementation, after the exercise consumption data is transmitted to the application server, the exercise consumption data may be periodically synchronized to the corresponding application client during exercise, or may be synchronized to the application client after the exercise ends, or an operation of synchronizing the exercise consumption data to the application client may be performed when the user initiates a synchronization request.

In addition, even if a version of the application client is not updated, the exercise consumption data is not lost with the data synchronization method provided in this embodiment. Specifically, when a new data type is recorded on the exercise device 200, for example, a foot landing time is newly recorded, the newly added data is synchronized and stored to the application server even if a corresponding version update is not performed on the application client. After the corresponding update is performed on the application client, and the application client has a function of recording the newly added data, all data recorded since the exercise device 200 started to record the newly added data is found on the application server and synchronized to the updated application client. This ensures integrity of exercise data, and improves an intelligent level of recording the exercise data, thereby improving user experience.

It should be noted that, after step 505, the exercise consumption data may be not only displayed on the first display unit 204 of the exercise device 200, but also fed back to the application client on the user terminal 400. A specific manner and location of displaying the obtained exercise consumption data are not specifically limited in this embodiment of this application.

It can be learned that, in this embodiment of this application, when the user needs to use the exercise device 200 for exercise, the exercise device 200 may receive the user information from the exercise device server 300 corresponding to the exercise device. The user information is obtained from the application server corresponding to the application client by the exercise device server 300 based on the user identifier provided by the application client corresponding to the user terminal 400. In addition, the user information is entered and recorded by the user on the user terminal 400 and synchronized to the application server. In this case, the exercise device 200 may calculate the exercise consumption data of the user based on the recorded exercise parameter and with reference to the received user information. In this way, by using an inherent connection relationship between the exercise device 200 and the corresponding exercise device server 300, and the established connection between the exercise device server 300 and the application server corresponding to the application client, the exercise device 200 can obtain the user information recorded on the application client on the user terminal 400, so that the exercise device 200 can specifically calculate accurate exercise consumption data of the user, and the user does not need to manually enter the user information on the exercise device 200 during exercise, thereby facilitating processing of exercise data of the user on the exercise device 200, and improving exercise experience of the user.

After the exercise data processing method corresponding to the first possible implementation is described, the following specifically describes an exercise data processing method corresponding to the second possible implementation.

Figure 8:
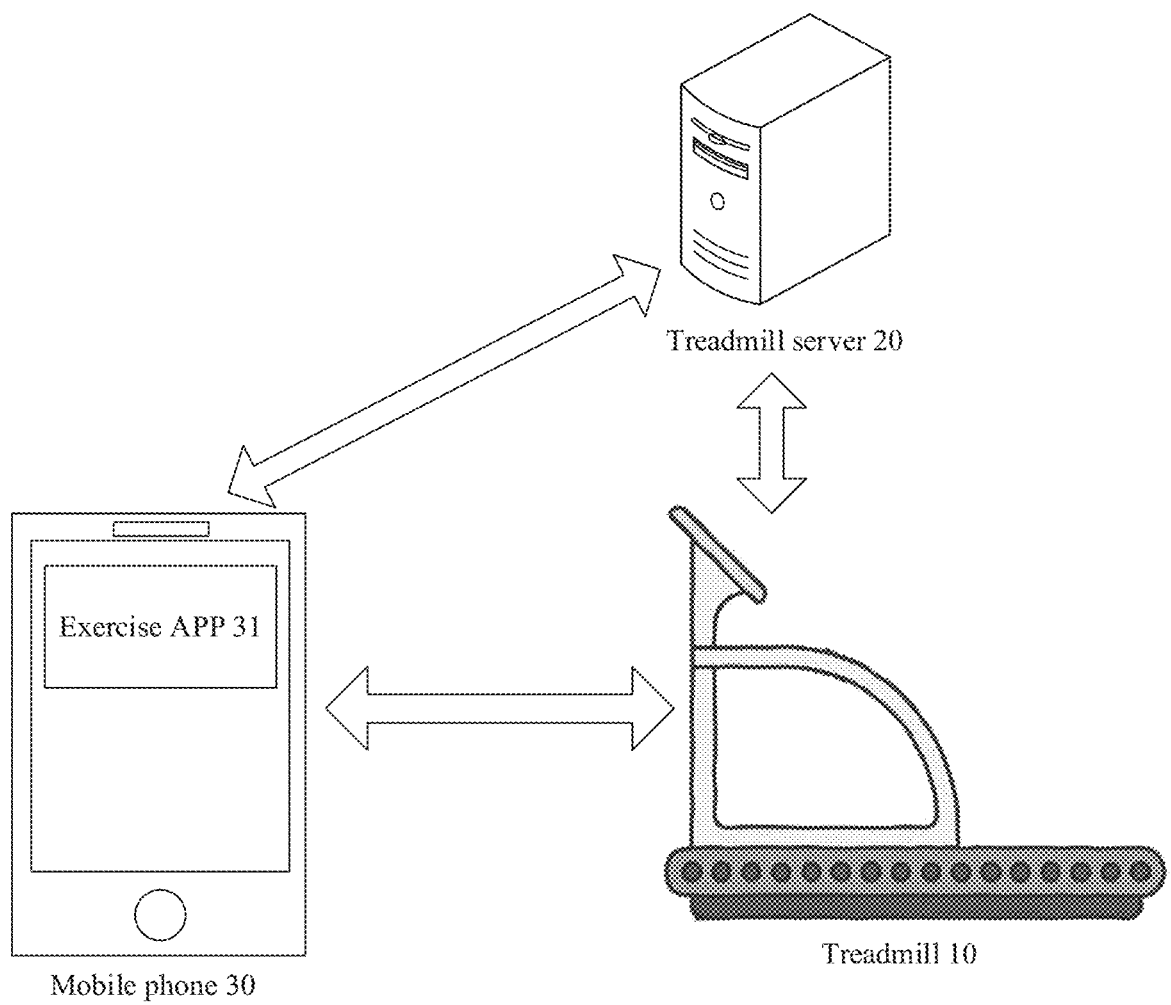
FIG. 8 is a schematic diagram of a system framework in another application scenario according to an embodiment of this application.

For example, in a scenario in the embodiments of this application, the second possible implementation may be used in a scenario shown in FIG. 8. In the scenario, the exercise device is a treadmill 10, the exercise device server is a treadmill server 20 corresponding to the treadmill 10, the user terminal is a mobile phone 30 of a user, and the application client is an exercise APP 31 installed on the mobile phone 30. After the user downloads and installs the exercise APP 31 on the mobile phone 30, when registering an account or completing personal information, the user may enter and store user information of the user, for example, information such as an age, a gender, a height, and a weight. In addition, an information code (for example, a two-dimensional code) may be further displayed on the treadmill 10, so that the user can obtain information when using the treadmill 10.

A specific exercise data processing solution may include: A user A wants to use the treadmill 10. First, the user A powers on the treadmill 10, and scans the information code on the treadmill 10 by using the exercise APP 31 on the mobile phone 30, so that the exercise APP 31 obtains a device identifier aaaa of the treadmill 10. Then the exercise APP 31 determines, by using the aaaa, that a to-be-used treadmill is the treadmill 10, and requests Bluetooth pairing information of the treadmill 10 from the treadmill server 20 corresponding to the treadmill 10. Then the treadmill server 20 sends the Bluetooth pairing information cccc of the treadmill 10 to the exercise APP 31, so that the mobile phone 30 generates a Bluetooth pairing request based on the cccc, and sends the Bluetooth pairing request to the treadmill 10, to establish a Bluetooth connection to the treadmill 10. The treadmill 10 may directly obtain user information bbbb from the exercise APP 31. Finally, the treadmill 10 processes, based on the user information bbbb, an exercise parameter of A that is collected in real time, to obtain real-time exercise consumption data of A until A completes running on the treadmill 10. The treadmill 10 generates total exercise consumption data of A for the running.

It should be noted that the treadmill server 20 in the scenario is a network-side management device corresponding to the treadmill 10, and may be a specific service device, or may be a cloud service device. Similarly, an APP server 40 is a network-side management device corresponding to the exercise APP 31, and may be a specific service device, or may be a cloud service device. This is not specifically limited in this embodiment of this application.

It can be understood that the foregoing scenario is merely an example of a scenario provided in the embodiments of this application, and the embodiments of this application are not limited to the scenario.

Figure 9:
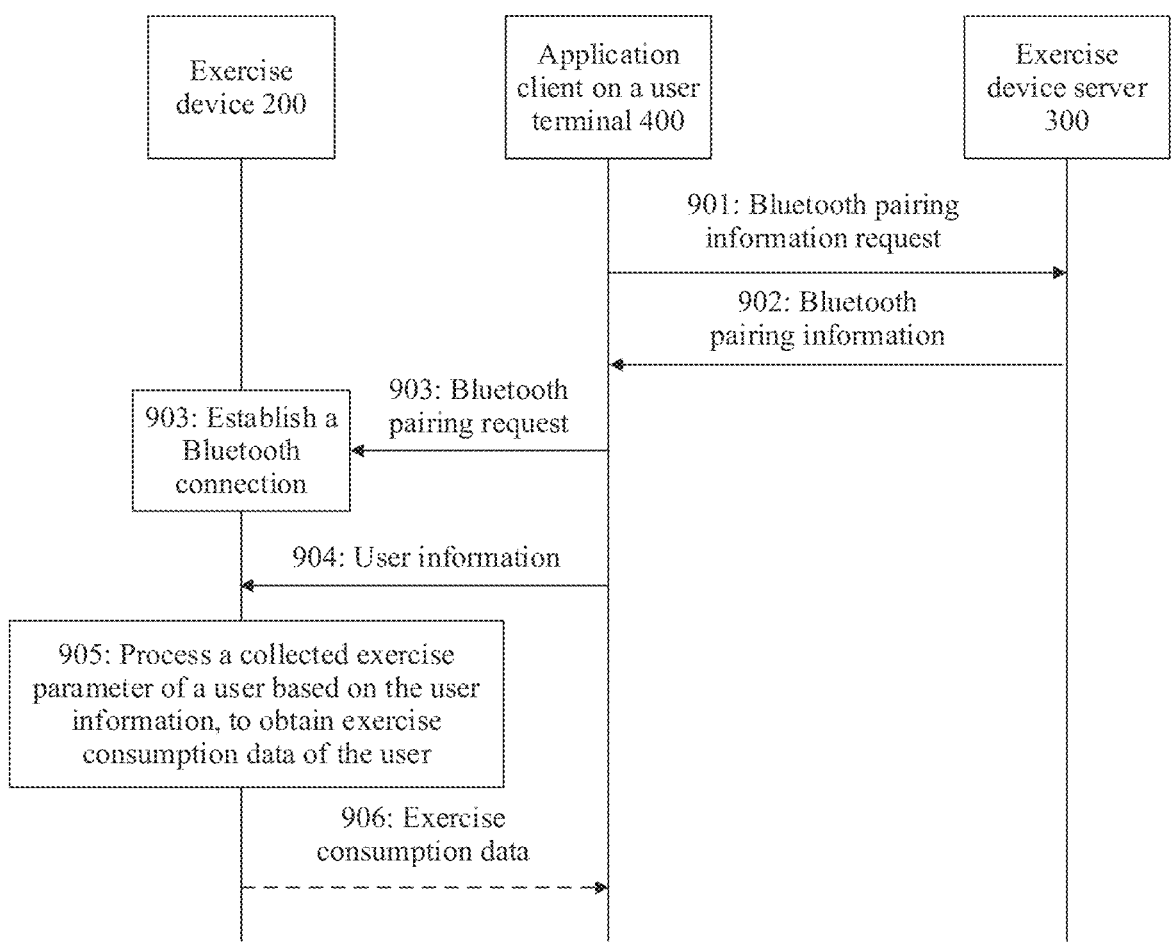
FIG. 9 is a signaling flowchart of another exercise data processing method according to an embodiment of this application.

FIG. 9 is a schematic signaling flowchart of an exercise data processing method according to an embodiment of this application. Referring to FIG. 9, the exercise data processing method corresponds to the second possible implementation, and specifically includes step 901 to step 905.

Step 901: An application client on a user terminal 400 requests, based on a device identifier of an exercise device 200 to be used by a user, Bluetooth pairing information corresponding to the exercise device 200 from an exercise device server 300 corresponding to the exercise device 200.

It can be understood that step 901 may be specifically as follows: A transceiver 403 of the user terminal 400 requests, based on the device identifier of the exercise device 200 to be used by the user, the Bluetooth pairing information corresponding to the exercise device 200 from the exercise device server 300 corresponding to the exercise device 200. A transceiver 303 of the exercise device server 300 may receive the request.

During specific implementation, when the user needs to use the exercise device 200 for exercise, step 901 may specifically include: Step 1: The user may power on the exercise device 200 by tapping a power-on button of the exercise device 200 or the like. Step 2: The user may obtain the device identifier of the exercise device 200 by using the application client installed on the user terminal 400 of the user. Step 3: The application client determines the to-be-used exercise device 200 based on the obtained device identifier, and generates a Bluetooth pairing information obtaining request based on a user identifier and an application client identifier. Step 4: The application client sends the Bluetooth pairing information obtaining request to the exercise device server 300 corresponding to the determined to-be-used exercise device 200.

It can be understood that the Bluetooth pairing information specifically includes a version number, a used protocol, a MAC address of the exercise device, and the like. Different exercise devices 200 correspond to different Bluetooth pairing information. The Bluetooth pairing information may be information sent by the exercise device server 300 to the user terminal 400 after the user terminal 400 scans an information code displayed on the exercise device 200 and is connected to the exercise device server 300 corresponding to the exercise device 200.

When obtaining the device identifier of the exercise device 200, the application client may determine, based on the device identifier, the exercise device 200 that the user currently wants to use, and may also determine a receiver of the Bluetooth pairing information obtaining request generated by the application client, that is, the exercise device server 300 corresponding to the exercise device 200. The Bluetooth pairing information obtaining request carries the device identifier of the exercise device 200, and is used to request the exercise device server 300 to feed back the Bluetooth pairing information corresponding to the device identifier.

It should be noted that, for a manner of triggering the request and a manner of obtaining the device identifier in step 901, refer to the related descriptions in step 501 in the embodiment shown in FIG. 5. Details are not described herein again.

Step 902: The exercise device server 300 sends, to the user terminal 400, the Bluetooth pairing information corresponding to the exercise device 200.

It can be understood that step 902 may be specifically as follows: The transceiver 303 of the exercise device server 300 sends, to the user terminal 400, the Bluetooth pairing information corresponding to the exercise device 200. The transceiver 403 of the user terminal 400 receives the Bluetooth pairing information.

Step 903: The user terminal 400 sends a Bluetooth pairing request to the exercise device 200, and establishes a Bluetooth connection to the exercise device 200. The Bluetooth pairing request is generated by the user terminal 400 based on the Bluetooth pairing information of the exercise device.

It can be understood that step 903 may be specifically as follows: The transceiver 403 of the user terminal 400 sends the Bluetooth pairing request to the exercise device 200. A transceiver 203 of the exercise device 200 receives the Bluetooth pairing request, and establishes the Bluetooth connection to the user terminal 400 by using a Bluetooth module 206.

It can be understood that the Bluetooth pairing request may be a message that is generated based on the Bluetooth pairing information of the exercise device 200 and that is used to request to establish the Bluetooth connection.

During specific implementation, after receiving the Bluetooth pairing information obtaining request, the exercise device server 300 may first determine the exercise device 200 corresponding to the device identifier, then search for the Bluetooth pairing information corresponding to the exercise device 200, and then send the found Bluetooth pairing information to the user terminal 400. Then the user terminal 400 generates the Bluetooth pairing request based on the received Bluetooth pairing information, and initiates a Bluetooth connection request to the determined exercise device 200. Finally, the exercise device 200 receives the Bluetooth connection request, and establishes the Bluetooth connection to the user terminal 400.

Step 904: The user terminal 400 sends user information to the exercise device 200 through the Bluetooth connection.

It can be understood that step 904 may be specifically as follows: The transceiver 403 of the user terminal 400 sends the user information to the exercise device 200.

Step 905: The exercise device 200 processes a collected exercise parameter of the user based on the user information, to obtain exercise consumption data of the user.

It can be understood that step 905 may be specifically as follows: After the transceiver 203 of the exercise device 200 receives the user information sent by the user terminal 400, a processor 202 of the exercise device 200 processes the collected exercise parameter of the user based on the user information, to obtain the exercise consumption data of the user.

It can be understood that, to ensure that the user can control distribution of the user information of the user, the user terminal 400 needs to obtain an indication from the user before sending the user information to the exercise device through the Bluetooth connection. If the user uses the exercise device 200 for exercise, when the exercise device 200 requests the user information from the application client, first, it may be determined whether the user uses the exercise device 200 for the first time. If yes, the user may be guided by using a standard authorization procedure (for example, an Oauth 2.0 authorization procedure) to perform authorization on the application client of the user according to willingness of the user, and the user information is determined in information about user authorization allowed during the authorization, and is sent to the exercise device 200. If the user uses the exercise device 200 not for the first time, that is, the user has performed authorization on the application client of the user, the application client may determine the user information based on the existing authorization, and send the user information to the exercise device 200. In this way, the user information of the user may be shared under awareness of the user, thereby ensuring that the user can protect personal information of the user, and improving user experience on a basis of protecting user privacy.

It should be noted that step 904 and step 905 differ from step 504 and step 505 in the embodiment shown in FIG. 5 only in a connection based on which user data is sent. In this embodiment, the user information is transmitted based on the established Bluetooth connection, and in the embodiment corresponding to FIG. 5, the user information is transmitted through the inherent connection between the exercise device server 300 and the exercise device 200. Therefore, for implementations of step 904 and step 905, refer to the related descriptions of step 504 and step 505 in the embodiment shown in FIG. 5. Details are not described herein again.

It can be understood that, after step 905, to display comparatively accurate exercise consumption data obtained through processing to the user, in an example, a display manner may include: The exercise device 200 may directly display the exercise consumption data on a first display unit 205, that is, a display of the exercise device 200 or an external display device connected to the exercise device 200, until the user stops using the exercise device and powers off the exercise device. In another example, to help the user conveniently record exercise data by using the application client, and ensure comprehensiveness of the exercise data, a display manner may alternatively include the following step:

Step 906: The exercise device 200 sends the exercise consumption data to the application client through the Bluetooth connection.

It can be understood that step 906 may be specifically as follows: The transceiver 203 of the exercise device 200 sends the exercise consumption data to the application client on the user terminal 400.

During specific implementation, exercise consumption data calculated by the exercise device 200 in real time may be periodically synchronized to the corresponding application client during exercise, or may be synchronized to the application client after the exercise ends. It should be noted that, after step 905, the exercise consumption data may be not only displayed on the first display unit 205 of the exercise device 200, but also fed back to the application client on the user terminal 400. A specific manner and location of displaying the obtained exercise consumption data are not specifically limited in this embodiment of this application.

It should be noted that, in this embodiment of this application, the exercise device 200 needs to have a Bluetooth communication function and support a Bluetooth connection and a Bluetooth protocol. In addition, the user needs to turn on a Bluetooth function of a Bluetooth module 405 on the user terminal 400.

It can be learned that, in this embodiment of this application, when the user needs to use the exercise device 200 for exercise, the exercise device 200 may receive the Bluetooth pairing request sent by the user terminal 400, and establish the Bluetooth connection to the user terminal 400. The Bluetooth pairing request is generated by the user terminal 400 based on the Bluetooth pairing information of the exercise device 200. Then the exercise device 200 obtains, through the established Bluetooth connection, the user information sent by the application client on the user terminal 400. In this case, the exercise device 200 may calculate the exercise consumption data of the user based on a recorded exercise parameter and with reference to the received user information. In this way, the Bluetooth connection is established between the exercise device 200 and the user terminal 400, so that the exercise device 200 can obtain the user information recorded by the user on the application client on the user terminal 400, the exercise device 200 can specifically calculate accurate exercise consumption data of the user, and the user does not need to manually enter the user information on the exercise device 200 during exercise, thereby facilitating processing of exercise data of the user on the exercise device 200, and improving exercise experience of the user.

Figure 10:
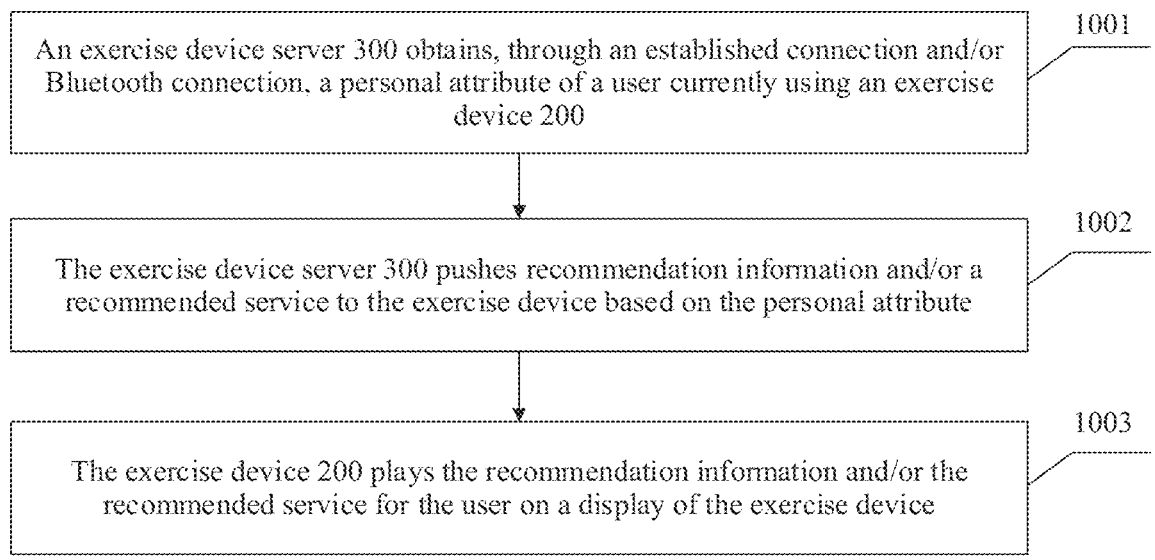
FIG. 10 is a schematic flowchart of an example of another exercise data processing method according to an embodiment of this application.

In addition, in this embodiment of this application, to improve experience of using the exercise device, based on the first possible implementation and/or the second possible implementation, as shown in FIG. 10, an implementation of pushing, in a personalized manner, recommendation information and/or a recommended service to a user doing exercise is further provided. The implementation is specifically applicable to the exercise device 200 that has the display or is connected to the external display device. A specific implementation process includes the following steps.

Step 1001: The exercise device server 300 obtains, through the established connection and/or Bluetooth connection, a personal attribute of the user currently using the exercise device 200.

It can be understood that step 1001 may be specifically as follows: The transceiver 303 of the exercise device server 300 obtains, through the established connection and/or Bluetooth connection, the personal attribute of the user currently using the exercise device 200.

The personal attribute may be specifically personal information such as a gender, an age, or an occupation of the user.

During specific implementation, the exercise device server 300 may obtain the personal attribute according to the manner of obtaining the user information in the first possible implementation. For a specific implementation, refer to the related descriptions in the embodiment shown in FIG. 5.

Alternatively, the exercise device server 300 may obtain the personal attribute according to the manner of obtaining the user information in the second possible implementation. A specific process may be as follows: The exercise device 200 obtains the personal attribute from the application client through the Bluetooth connection, and then sends the personal attribute to the exercise device server 300. For a specific implementation, refer to the related descriptions in the embodiment shown in FIG. 9.

Step 1002: The exercise device server 300 pushes recommendation information and/or a recommended service to the exercise device 200 based on the personal attribute.

It can be understood that step 1002 may be specifically as follows: The processor 302 of the exercise device server 300 determines the recommendation information and/or the recommended service based on the personal attribute, and drives the transceiver 303 of the exercise device server 300 to push the recommendation information and/or the recommended service to the exercise device 200.

For example, for a female aged 20 to 30 years old, post-exercise skincare products and application methods may be pushed to the exercise device 200. For another example, for a male aged 30 to 50 years old, current affairs and political news may be pushed to the exercise device 200. For still another example, for a user above 50 years old, health preservation methods and fitness precautions may be pushed to the exercise device 200.

Step 1003: The exercise device 200 plays the recommendation information and/or the recommended service for the user on the second display unit 205 of the exercise device 200.

In this way, the exercise device server 300 can automatically obtain the personal attribute of the user, analyze and predict possible interests and preferences of the user based on the personal attribute, and specifically provide the recommendation information and/or the recommended service to the exercise device 200, thereby improving the user's interest in exercise. This not only facilitates promotion of national fitness, but also improves user experience when the user uses the exercise device 200.

In addition, during specific implementation, both the first possible implementation and the second possible implementation may be configured on one exercise device. In this case, after a user obtains a device identifier of the exercise device by using an application client on a user terminal, the device identifier may be displayed on a display of the exercise device, an external display device connected to the exercise device, or the application client, for the user to select a connection mode: a server connection or a Bluetooth connection. When the user selects the server connection, the embodiment corresponding to FIG. 5 is performed. When the user selects the Bluetooth connection, the embodiment corresponding to FIG. 9 is performed. In this way, participation of the user in using the exercise device is improved, and user experience when the user uses the exercise device is improved.

It should be noted that an embodiment of this application further provides an exercise data processing method, specifically including: After a user manually enters user information or an exercise device obtains user information in the first possible implementation or the second possible implementation, and the exercise device obtains exercise consumption data through calculation, the user may transmit, through a connection established in the first possible implementation or a Bluetooth connection established in the second possible implementation, the exercise consumption data to an application client that is on a user terminal and that is used to record exercise data. In this way, the following problem is resolved: The exercise consumption data of the user that is generated after exercise exists only on the exercise device. If the user wants to record the exercise consumption data on the application client, the user needs to manually enter the exercise consumption data. This not only results in complex and time-consuming operations, but also easily causes loss of some exercise data (for example, only calories consumed during running are recorded, but exercise data such as a foot landing location or force exerting duration is not recorded).

In addition, for the embodiment corresponding to FIG. 5 and the embodiment corresponding to FIG. 9, this embodiment of this application further includes: The user may use the connection established in the first possible implementation or the Bluetooth connection established in the second possible implementation. Then, in a case, the exercise device sends a collected exercise parameter to an exercise device server of the exercise device through the established connection or Bluetooth connection. The exercise device server obtains the exercise consumption data based on the obtained user information and exercise parameter. Then the exercise device server sends the exercise consumption data to the exercise device for display on a display of the exercise device or an external display device connected to the exercise device, and sends the exercise consumption data to the corresponding application client for display. In another case, the exercise device sends a collected exercise parameter to the application client through the established connection or Bluetooth connection. The application client obtains the exercise consumption data based on the recorded user information and the received exercise parameter. The application client displays the exercise consumption data, and sends the exercise consumption data to the exercise device for display on a display of the exercise device or an external display device connected to the exercise device.

After the technical solutions in the embodiments of this application are described, to make the embodiments of this application clearer, the following describes, with reference to the accompanying drawings, a specific example corresponding to the embodiments of this application.

Figure 11:
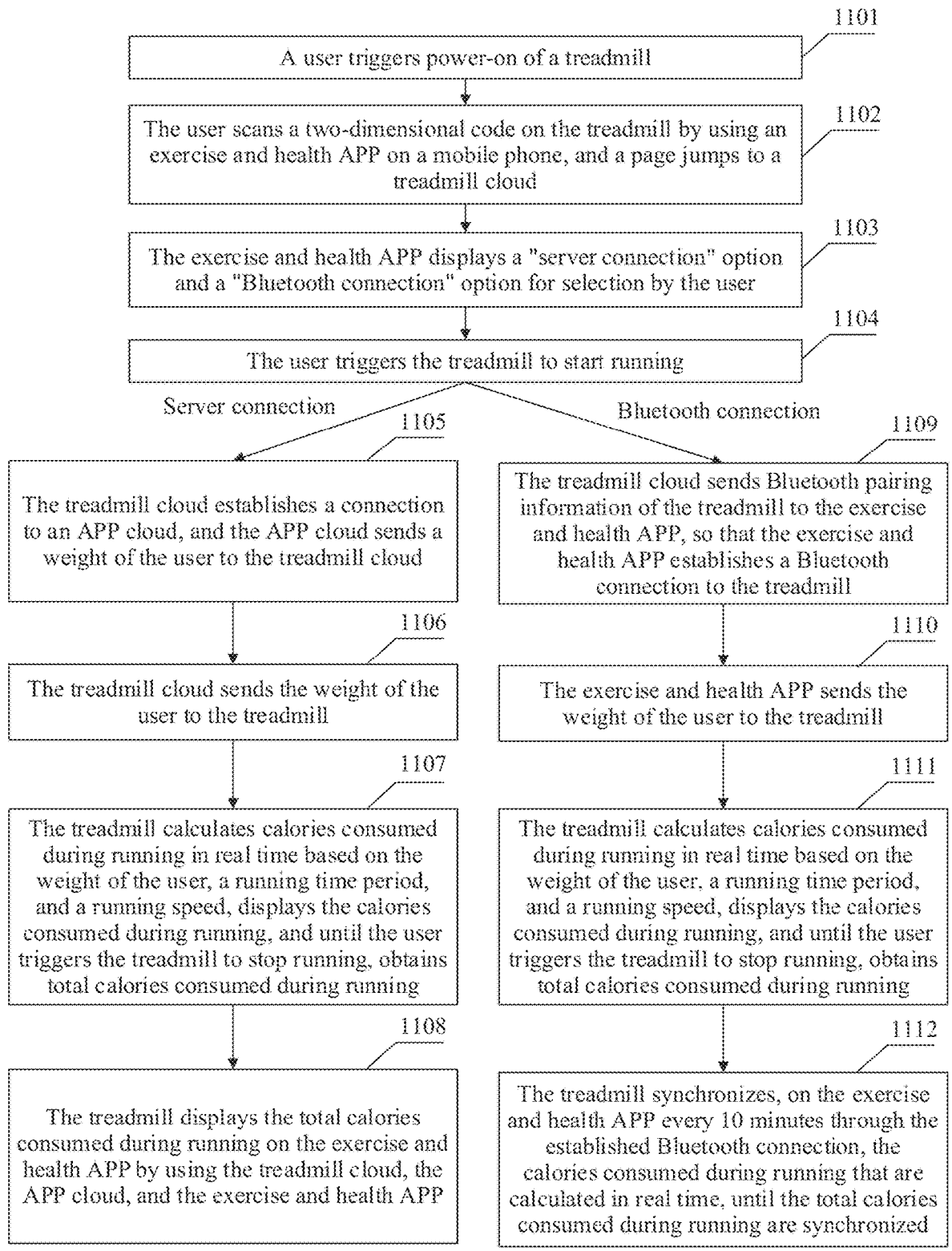
FIG. 11 is a schematic flowchart of a scenario of an exercise data processing method according to an embodiment of this application.

Referring to FIG. 11, in this example, the exercise device is a treadmill, the exercise device server is a treadmill cloud corresponding to the treadmill, the user terminal is a mobile phone of a user, the application client is an exercise and health APP installed on the mobile phone, and the application server is an APP cloud. The treadmill has a display, and the treadmill displays a two-dimensional code after power-on. The exercise consumption data is calories consumed during running. The exercise parameter includes a running time period and a running speed. The user information includes a weight. The personal attribute includes a gender and an age. This embodiment of this application may specifically include the following steps.

Step 1101: The user triggers power-on of the treadmill.

Step 1102: The user scans the two-dimensional code on the treadmill by using the exercise and health APP on the mobile phone, and a page jumps to the treadmill cloud.

Step 1103: The exercise and health APP displays a "server connection" option and a "Bluetooth connection" option for selection by the user. When the user selects the "server connection", step 1105 to step 1108 are performed. When the user selects the "Bluetooth connection", step 1109 to step 1112 are performed.

Step 1104: The user triggers the treadmill to start running.

Step 1105: The treadmill cloud establishes a connection to the APP cloud, and the APP cloud sends the weight of the user to the treadmill cloud.

Step 1106: The treadmill cloud sends the weight of the user to the treadmill.

It should be noted that a sequence for performing step 1104 and performing step 1105 to step 1106 is not limited in this embodiment of this application.

Step 1107: The treadmill calculates calories consumed during running in real time based on the weight of the user, a running time period, and a running speed, displays the calories consumed during running, and until the user triggers the treadmill to stop running, obtains total calories consumed during running.

Step 1108: The treadmill displays the total calories consumed during running on the exercise and health APP by using the treadmill cloud, the APP cloud, and the exercise and health APP.

Step 1109: The treadmill cloud sends Bluetooth pairing information of the treadmill to the exercise and health APP, so that the exercise and health APP establishes a Bluetooth connection to the treadmill.

Step 1110: The exercise and health APP sends the weight of the user to the treadmill.

Step 1111: The treadmill calculates calories consumed during running in real time based on the weight of the user, a running time period, and a running speed, and displays the calories consumed during running, until the user triggers the treadmill to stop running; and obtains total calories consumed during running.

Step 1112: The treadmill synchronizes, on the exercise and health APP every 10 minutes through the established Bluetooth connection, the calories consumed during running that are calculated in real time, until the total calories consumed during running are synchronized.

It can be learned that, according to the exercise data processing method provided in this embodiment of this application, the user may record and store the user information on the application client installed on the user terminal of the user. In this case, when the user needs to use the exercise device for exercise, the exercise device may automatically obtain the user information of the user, and the user does not need to manually enter the user information each time when using the exercise device. This not only ensures security of the user's personal information, but also can specifically calculate and output accurate exercise consumption data of the user, thereby improving user experience when the user uses the exercise device for exercise.

The "first" in the names such as the "first Bluetooth module" and the "first display unit" mentioned in the embodiments of this application is merely used as a name identifier, but does not indicate the first in order. This rule is also applicable to the "second", and the like.

From the foregoing descriptions of the implementations, a person skilled in the art may clearly understand that some or all steps of the methods in the embodiments may be implemented by software in addition to a universal hardware platform. Based on such an understanding, the technical solutions of this application may be implemented in a form of a software product. The software product may be stored in a storage medium, such as a read-only memory (English: read-only memory, ROM)/RAM, a magnetic disk, or an optical disc, and includes several instructions for instructing a computer device (which may be a personal computer, a server, or a network communications device such as a router) to perform the methods described in the embodiments or some parts of the embodiments of this application.

The embodiments in this specification are all described in a progressive manner, for same or similar parts in the embodiments, refer to these embodiments, and each embodiment focuses on a difference from other embodiments. Especially, an apparatus embodiment is basically similar to a method embodiment, and therefore is described briefly; for related parts, refer to partial descriptions in the method embodiment. The described apparatus embodiment is merely an example. The modules described as separate parts may or may not be physically separate, and parts displayed as modules may or may not be physical modules, may be located in one position, or may be distributed on a plurality of network units. Some or all the modules may be selected according to actual requirements to achieve the objectives of the solutions of the embodiments. A person of ordinary skill in the art may understand and implement the embodiments of the present invention without creative efforts.

The foregoing descriptions are merely example implementations of this application, but are not intended to limit the protection scope of this application.

What is claimed is:

1. An exercise device comprising:
 a memory configured to store instructions; and
 a processor coupled to the memory, wherein the instructions cause the processor to be configured to:
  obtain, from an exercise device server corresponding to a device identifier of the exercise device, user information corresponding to a user of the exercise device, wherein the user information is based on recordation from the user on an application client of a user terminal, synchronization to an application server based on an application server identifier corresponding to the application client, and communication from the application server to the exercise device server in response to triggering by the application client; and
  process, based on the user information, a collected exercise parameter of the user to obtain exercise consumption data of the user.

2. The exercise device of claim 1, wherein the memory is further configured to store an information code configured to enable the user terminal to obtain the device identifier of the exercise device and couple to the exercise device server corresponding to the device identifier.

3. The exercise device of claim 1, wherein the instructions further cause the processor to be configured to send the exercise consumption data to the exercise device server to enable the exercise device server to send the exercise consumption data to the application client using the application server.

4. The exercise device of claim 1, further comprising a first display, wherein the instructions further cause the processor to be configured to display, using the first display, the exercise consumption data.

5. The exercise device of claim 1, further comprising a second display, wherein the instructions further cause the processor to be configured to:
receive, through an established connection and from the exercise device server, recommendation information and a recommended service based on a personal attribute of the user, wherein the personal attribute is obtained by the exercise device server from the application server based on the established connection; and
display, using the second display, the recommendation information and the recommended service.

6. The exercise device of claim 1, further comprising a second display, wherein the instructions further cause the processor to be configured to:
receive, through an established connection and from the exercise device server, recommendation information based on a personal attribute of the user, wherein the personal attribute is obtained by the exercise device server from the application server based on the established connection; and
display, using the second display, the recommendation information and/or the recommended service.

7. An exercise device server comprising:
a memory configured to store instructions; and
a processor coupled to the memory, wherein the instructions cause the processor to be configured to:
receive, from an application client on a user terminal and based on a device identifier of the exercise device, a connection request corresponding to an exercise device, wherein the connection request carries a user identifier and an application server identifier corresponding to the application client;
establish a connection to an application server corresponding to the application server identifier;
obtain, based on the connection from the application server, user information corresponding to the user identifier, wherein the user information is based on recordation from a user on the application client of the user terminal and synchronization to the application server corresponding to the application client; and
send the user information to the exercise device to enable the exercise device to process, based on the user information, a collected exercise parameter of the user to obtain exercise consumption data of the user.

8. The exercise device server of claim 7, wherein the instructions further cause the processor to be configured to:
identify the application server after receiving the connection request; and
establish the connection to the application server when an authorization relationship exists between a first operator corresponding to the exercise device server and a second operator corresponding to the application server.

9. The exercise device server of claim 7, wherein the instructions further cause the processor to be configured to:

receive the exercise consumption data from the exercise device; and
send, using the application server, the exercise consumption data to the application client.

10. The exercise device server of claim 9, wherein the instructions further cause the processor to be configured to:
determine a target application server identifier corresponding to the exercise device;
establish the connection to the application server corresponding to the target application server identifier; and
send the exercise consumption data to the application server to enable the application server to forward the exercise consumption data to the application client.

11. The exercise device server of claim 7, wherein the instructions further cause the processor to be configured to:
obtain, through the connection, a personal attribute of the user; and
push recommendation information and a recommended service to the exercise device based on the personal attribute to enable the exercise device to display the recommendation information and the recommended service for the user on a display.

12. The exercise device server of claim 7, wherein the instructions further cause the processor to be configured to:
obtain, through the connection, a personal attribute of the user; and
push recommendation information to the exercise device based on the personal attribute to enable the exercise device to display the recommendation information and/or the recommended service for the user on a display.

13. The exercise device server of claim 12, wherein the personal attribute comprises a gender of the user.

14. The exercise device server of claim 12, wherein the personal attribute comprises an age of the user.

15. The exercise device server of claim 12, wherein the personal attribute comprises an occupation of the user.

16. An exercise device comprising:
a memory configured to store instructions; and
a processor coupled to the memory, wherein the instructions cause the processor to be configured to:
receive, from a user terminal, a BLUETOOTH pairing request that is based on BLUETOOTH pairing information of the exercise device;
establish a BLUETOOTH connection to the user terminal in response to the BLUETOOTH pairing request;
obtain, through the BLUETOOTH connection and from the user terminal, user information, wherein the user information is based on recordation from a user on an application client of the user terminal, synchronization to an application server based on a device identifier of the exercise device and an application server identifier corresponding to the application client, and communication from the application server to an exercise device server in response to triggering by the application client; and
process a collected exercise parameter of the user based on the user information to obtain exercise consumption data of the user.

17. The exercise device of claim 16, wherein the memory is further configured to store an information code configured to enable the user terminal to obtain the device identifier of the exercise device, to couple to the exercise device server corresponding to the device identifier, and to obtain the BLUETOOTH pairing information from the exercise device server.

18. The exercise device of claim 16, wherein the instructions further cause the processor to be configured to send the exercise consumption data to the application client through the BLUETOOTH connection.

19. The exercise device of claim 16, further comprising a first display, wherein after obtaining the exercise consumption data, the instructions further cause the processor to be configured to display, using the first display, the exercise consumption data.

20. The exercise device of claim 16, further comprising a second display, wherein the instructions further cause the processor to be configured to:
- obtain, from the application client through the BLUETOOTH connection, a personal attribute of the user;
- request, based on the personal attribute, the exercise device server to push recommendation information and a recommended service; and
- display, using the second display, the recommendation information and/or the recommended service.

* * * * *